(12) United States Patent
Noertker et al.

(10) Patent No.: US 9,712,907 B2
(45) Date of Patent: Jul. 18, 2017

(54) METHODS OF GENERATING TACTILE USER FEEDBACK UTILIZING HEADPHONE DEVICES AND RELATED SYSTEMS

(71) Applicant: Skullcandy, Inc., Park City, UT (US)

(72) Inventors: Sam Noertker, Park City, UT (US); John Timothy, Salt Lake City, UT (US); Matthew Windt, Heber City, UT (US)

(73) Assignee: Skullcandy, Inc., Park City, UT (US)

( * ) Notice: Subject to any disclaimer, the term of this patent is extended or adjusted under 35 U.S.C. 154(b) by 0 days.

(21) Appl. No.: 14/982,647

(22) Filed: Dec. 29, 2015

(65) Prior Publication Data

US 2016/0192060 A1    Jun. 30, 2016

Related U.S. Application Data

(60) Provisional application No. 62/098,936, filed on Dec. 31, 2014.

(51) Int. Cl.
*H04R 1/10* (2006.01)
*H04R 29/00* (2006.01)
(Continued)

(52) U.S. Cl.
CPC ......... *H04R 1/1075* (2013.01); *A61B 5/7455* (2013.01); *G06F 3/016* (2013.01);
(Continued)

(58) Field of Classification Search
CPC H04R 2400/03; H04R 1/1075; H04R 1/1008; H04R 29/001; G06F 3/016; A61B 5/7455
See application file for complete search history.

(56) References Cited

U.S. PATENT DOCUMENTS 6,377,145 B1   4/2002   Kumagai
6,603,863 B1   8/2003   Nagayoshi
(Continued)

FOREIGN PATENT DOCUMENTS

CA        153644 A      2/1914
CA       2515558 A1     2/2007
(Continued)

OTHER PUBLICATIONS

Anonymous, Current Divider, https://en.wikipedia.org/wiki/Current_divider, Nov. 23, 2014, 5 pages.
(Continued)

*Primary Examiner* — Muhammad N Edun
(74) *Attorney, Agent, or Firm* — TraskBritt (57) ABSTRACT

Methods of generating tactile user feedback utilizing headphone devices may involve sending a feedback signal from a computing device to a headphone device operatively connected to the computing device. A tactile vibration may be generated utilizing a tactile bass vibrator of the headphone device in response to the feedback signal. Systems for generating tactile user feedback utilizing headphone devices may include a headphone device operatively connected to a computing device, the headphone device comprising a tactile bass vibrator configured to generate a tactile vibration in response to a feedback signal received from the computing device. The computing device may be programmed to send a feedback signal to the headphone device in response to a predetermined event.

20 Claims, 3 Drawing Sheets

(51) Int. Cl.
*A61B 5/00* (2006.01)
*G06F 3/01* (2006.01)
*A61B 5/024* (2006.01)
*A61B 5/11* (2006.01)

(52) U.S. Cl.
CPC ......... H04R 1/1008 (2013.01); H04R 29/001 (2013.01); *A61B 5/02438* (2013.01); *A61B 5/1118* (2013.01); *A61B 5/486* (2013.01); *H04R 2400/03* (2013.01)

(56) References Cited

U.S. PATENT DOCUMENTS

| | | | |
|---|---|---|---|
| 6,850,138 | B1 | 2/2005 | Sakai |
| 7,187,948 | B2 | 3/2007 | Alden |
| 7,395,090 | B2 | 7/2008 | Alden |
| D623,627 | S | 9/2010 | Alden et al. |
| D624,057 | S | 9/2010 | Kelly et al. |
| D641,003 | S | 7/2011 | Alden |
| 3,014,824 | A1 | 9/2011 | Alden |
| D650,356 | S | 12/2011 | Alden et al. |
| D656,129 | S | 3/2012 | Kelly et al. |
| D665,776 | S | 8/2012 | Alden et al. |
| D665,777 | S | 8/2012 | Alden et al. |
| D673,136 | S | 12/2012 | Kelly et al. |
| D673,140 | S | 12/2012 | Kelly et al. |
| D674,372 | S | 1/2013 | Kelly et al. |
| D674,376 | S | 1/2013 | Kelly et al. |
| D676,023 | S | 2/2013 | Kelly et al. |
| D676,024 | S | 2/2013 | Kelly et al. |
| D677,241 | S | 3/2013 | Kelly et al. |
| D683,717 | S | 6/2013 | Kelly et al. |
| 8,457,557 | B2 | 6/2013 | Alden |
| D685,759 | S | 7/2013 | Kelly et al. |
| D685,767 | S | 7/2013 | Kelly et al. |
| 8,515,115 | B2 | 8/2013 | Kelly et al. |
| D689,464 | S | 9/2013 | Bonahoom et al. |
| 8,542,859 | B2 | 9/2013 | Alden |
| D691,582 | S | 10/2013 | Nguyen et al. |
| D693,793 | S | 11/2013 | Kelly et al. |
| 8,594,362 | B2 | 11/2013 | Liu |
| D699,216 | S | 2/2014 | Bonahoom et al. |
| D701,193 | S | 3/2014 | Kelly et al. |
| D701,196 | S | 3/2014 | Kelly et al. |
| D701,197 | S | 3/2014 | Kelly et al. |
| D707,654 | S | 6/2014 | Nguyen et al. |
| 8,767,996 | B1 | 7/2014 | Lin et al. |
| 8,942,403 | B2 | 1/2015 | Oman et al. |
| 8,965,028 | B2 | 2/2015 | Oishi et al. |
| 2004/0064066 | A1* | 4/2004 | John .................. A61B 5/04845 600/559 |
| 2006/0171553 | A1 | 8/2006 | Wong et al. |
| 2006/0262954 | A1 | 11/2006 | Lee et al. |
| 2007/0142025 | A1 | 6/2007 | Alden |
| 2008/0112581 | A1 | 5/2008 | Kim et al. |
| 2008/0267440 | A1 | 10/2008 | Alden |
| 2010/0239115 | A1 | 9/2010 | Richardson |
| 2010/0260371 | A1 | 10/2010 | Afshar |
| 2011/0075880 | A1 | 3/2011 | Kamimura et al. |
| 2011/0164776 | A1 | 7/2011 | Kelly et al. |
| 2011/0235819 | A1 | 9/2011 | Alden |
| 2011/0317856 | A1 | 12/2011 | Akasu |
| 2012/0087519 | A1 | 4/2012 | Emilsson |
| 2012/0128172 | A1 | 5/2012 | Alden |
| 2012/0275615 | A1 | 11/2012 | Kelly et al. |
| 2013/0051585 | A1 | 2/2013 | Karkkainen et al. |
| 2013/0118944 | A1 | 5/2013 | Niiro et al. |
| 2013/0130540 | A1 | 5/2013 | Oman et al. |
| 2013/0177165 | A1 | 7/2013 | Oishi |
| 2013/0177195 | A1 | 7/2013 | Sze et al. |
| 2013/0185905 | A1 | 7/2013 | Stiff et al. |
| 2013/0208909 | A1 | 8/2013 | Mulder |
| 2013/0225915 | A1* | 8/2013 | Redfield .............. A61N 5/0618 600/28 |
| 2013/0336514 | A1 | 12/2013 | Kelly et al. |
| 2014/0056459 | A1 | 2/2014 | Oishi et al. |
| 2014/0056463 | A1 | 2/2014 | Kim et al. |
| 2014/0168349 | A1 | 6/2014 | Eom et al. |
| 2014/0270228 | A1 | 9/2014 | Oishi et al. |
| 2014/0270230 | A1 | 9/2014 | Oishi et al. |
| 2016/0123745 | A1* | 5/2016 | Cotier .................. G09B 21/006 701/467 |

FOREIGN PATENT DOCUMENTS

| | | |
|---|---|---|
| CA | 2697029 A1 | 2/2007 |
| EP | 1760896 A1 | 3/2007 |
| EP | 1841278 A1 | 10/2007 |
| EP | 2262117 A1 | 12/2010 |
| EP | 2701400 A2 | 2/2014 |
| WO | 2010068495 A2 | 6/2010 |
| WO | 2010124190 A2 | 10/2010 |
| WO | 2011085096 A2 | 7/2011 |
| WO | 2012024656 A2 | 2/2012 |

OTHER PUBLICATIONS

European Search Report for European Application No. 15201843 dated Feb. 26, 2016, 7 pages.

Harris, Wayne, How to—Car Stereo—Nine Ways to Adjust Signal Level, http://www.termpro.com/asp/pubs.asp?ID=119, Jul. 1, 1990, 9 pages.

Timothy et al., Speaker Assemblies for Passive Generation of Vibrations and Related Headphone Devices and Methods, U.S. Appl. No. 14/982,786, filed Dec. 29, 2016.

* cited by examiner

METHODS OF GENERATING TACTILE USER FEEDBACK UTILIZING HEADPHONE DEVICES AND RELATED SYSTEMS

CROSS-REFERENCE TO RELATED APPLICATION

This application claims the benefit of U.S. Provisional Patent Application Ser. No. 62/098,936, filed Dec. 31, 2014. The subject matter of this application is related to the subject matter of U.S. Pat. No. 8,965,028, issued Feb. 24, 2015, and titled "SPEAKERS, HEADPHONES, AND KITS RELATED TO VIBRATIONS IN AN AUDIO SYSTEM, AND METHODS FOR FORMING SAME," the disclosure of each of which is incorporated in this application in its entirety by this reference.

FIELD

This disclosure relates generally to methods of generating tactile user feedback utilizing headphone devices, and systems including headphone devices configured to generate tactile user feedback. More specifically, disclosed embodiments relate to generating user feedback in ways that may be less intrusive than aural or visual feedback utilizing headphone devices configured to generate tactile user feedback.

BACKGROUND

Conventional portable audio systems often include a headphone that is connected to a media player (e.g., by one or more wires or by wireless technology). Conventional headphones may include one or more speaker assemblies having an audio driver that produces audible sound waves with a diaphragm. Such headphones may be connected to computing devices, such as, tablet devices, smartphones, video game consoles (e.g., portable video game consoles), and in-car infotainment systems. Such computing devices may provide user feedback, such as incoming text notifications or directions to follow a prescribed route, in the form of aural communications, which may be played over the headphones. Other devices connected to the computing devices, such as smart glasses and dash projectors, may provide user feedback in the form of visual communications displayed on such devices.

BRIEF SUMMARY

In some embodiments, the present disclosure includes methods of generating tactile user feedback utilizing a headphone device. In accordance with such methods, a feedback signal may be sent from a computing device to a headphone device operatively connected to the computing device. A tactile vibration may be generated utilizing a tactile bass vibrator of the headphone device in response to the feedback signal.

In additional embodiments, the present disclosure includes a system for generating tactile user feedback utilizing a headphone device. The system includes a headphone device operatively connected to a computing device. The headphone device has a tactile bass vibrator configured to generate a tactile vibration in response to a feedback signal received from the computing device, and the computing device is programmed to send a feedback signal to the headphone device in response to a predetermined event.

BRIEF DESCRIPTION OF THE DRAWINGS

While this disclosure concludes with claims particularly pointing out and distinctly claiming specific embodiments, various features and advantages of embodiments within the scope of this disclosure may be more readily ascertained from the following description when read in conjunction with the accompanying drawings, in which:

DETAILED DESCRIPTION

The illustrations presented in this disclosure are not meant to be actual views of any particular apparatus or component thereof, but are merely idealized representations employed to describe illustrative embodiments. Thus, the drawings are not necessarily to scale.

Disclosed embodiments relate generally to generating user feedback in ways that may be less intrusive than aural or visual feedback by utilizing headphone devices configured to generate tactile user feedback. More specifically, disclosed are embodiments of headphone devices including tactile bass vibrators that may generate tactile user feedback in response to receiving a feedback signal from a connected computing device.

A "speaker" is defined herein as an acoustic device configured to contribute to the generation of sound waves, such as with the reproduction of speech, music, or other audible sound. A speaker may also produce tactile vibrations that may be felt by a person. Thus, a speaker may include a tactile bass vibrator. A tactile bass vibrator may also be referred to as a transducer, a driver, a shaker, etc.

A "bass frequency" is a relatively low audible frequency generally considered to be within the range extending from approximately 16 Hz to approximately 512 Hz. For purposes of this disclosure, a "low bass frequency" refers to bass frequencies that may be felt as well as heard. Such low bass frequencies may be within the range extending from approximately 16 Hz to approximately 200 Hz.

Figure 1:
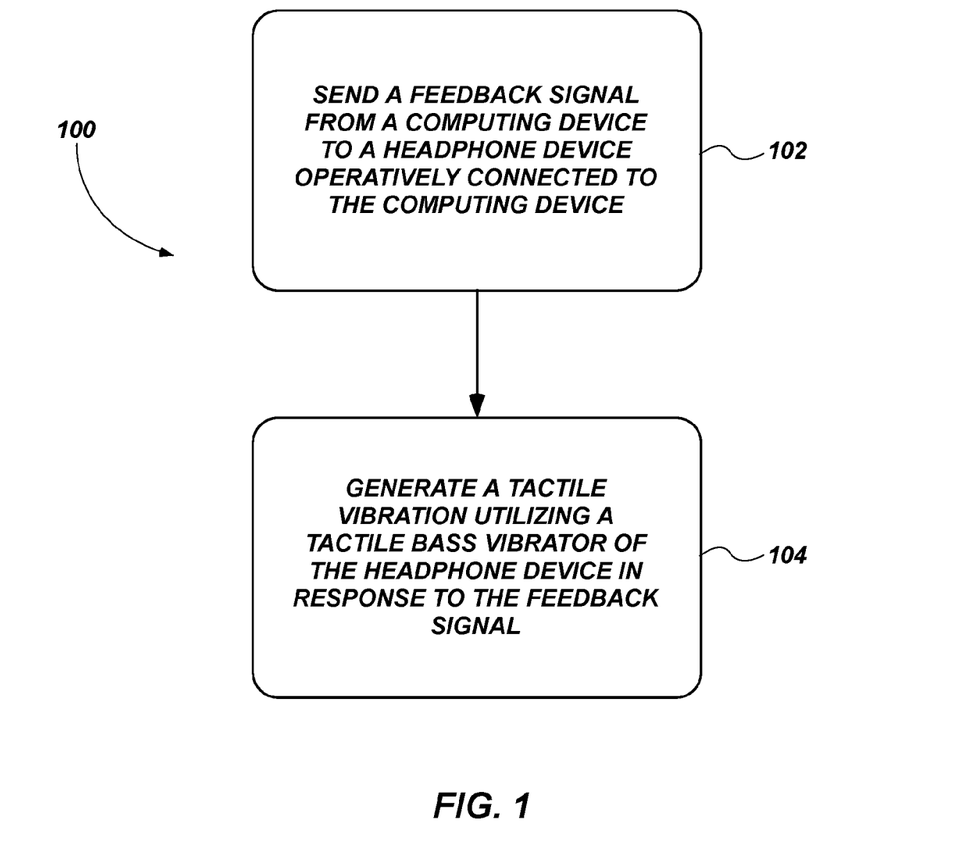
FIG. 1 is a flowchart diagram of a method of generating tactile user feedback utilizing a headphone device according to the present disclosure.

Referring to FIG. 1, a flowchart diagram of a method 100 of generating tactile (e.g., haptic) user feedback utilizing a headphone device is shown. The method 100 may involve sending a feedback signal from a computing device to a headphone device operatively connected to the computing device, as indicated at act 102. The feedback signal may be, for example, an audio signal from an audio file stored in memory of the computing device. In such an example, the feedback signal may be sent by any audio-enabled application running on the computing device. In other words, sending the feedback signal may not require installing a dedicated application on the computing device. The feedback signal may be, for example, an audio file composed of bass frequency waves. More specifically, the feedback signal may be, for example, an audio file composed of low bass frequency waves, in analog or digital format.

The feedback signal may be sent from the computing device to the headphone device in response to various inputs. The inputs may be generated by the computing device itself, by another device connected to the computing device (e.g., a peripheral or accessory), or by user input to the computing device. The inputs may relate to activities about which the user may desire feedback. For example, the inputs may relate to health information (e.g., heart rate, distance traveled while exercising, pace maintained while exercising, etc.), navigation information (e.g., distance to destination, turning and lane directions, distance traveled, etc.), or other activities a user may engage in while using the headphone device and computing device (e.g., sports activities, leisure activities, work activities, etc.). A feedback signal relating to any such input may be sent from the computing device to the headphone device.

As one example, the feedback signal may be sent from the computing device to the headphone device in response to a signal from a heart rate monitor of the computing device or operatively connected to the computing device. More specifically, the feedback signal may be sent from the computing device to the headphone device in response to a signal from a heart rate monitor indicating that a user's heart rate has exceeded a predetermined threshold or is within a predetermined range.

As another example, the feedback signal may be sent from the computing device to the headphone device in response to location information gathered by the computing device (e.g., utilizing a global positioning system (GPS) of the computing device). More specifically, the feedback signal may be sent from the computing device to the headphone device in response to traveling a predetermined distance, travelling at a calculated rate over a predetermined distance interval, or approaching a change of course in a predetermined route. In some embodiments, the feedback signal may be sent to a particular channel or a particular tactile bass vibrator of the headphone device. For example, the feedback signal may be sent to a left-side tactile bass vibrator or a right-side tactile bass vibrator of the headphone device corresponding to a direction in which a user is to turn to follow navigation directions.

As yet another example, the feedback signal may be sent from the computing device to the headphone device in response to a signal from an altimeter that a predetermined altitude threshold has been crossed. More specifically, the feedback signal may be sent from the computing device to the headphone device in response to descending past a threshold altitude beyond which deployment of a parachute is recommended.

As still another example, the feedback signal may be sent from the computing device to the headphone device in response to a user input received at the computing device. More specifically, the feedback signal may be sent from the computing device to the headphone device in response to user interaction with one or more user interface devices (e.g., buttons, switches, touchscreens, etc.) of the computing device.

Such feedback signals may convey useful information for, for example, exercise tracking, navigation, adventure sports, operation of the computing device, and other activities users may engage in while using the computing device and the headphone device. While certain illustrative examples have been given of inputs for sending feedback signals, those examples are not limiting. Feedback signals may be sent from the computing device to the headphone device in response to any input received, or generated, by the computing device.

In some embodiments, another audio signal may be sent from the computing device to the headphone device. The other audio signal may be distinct from the feedback signal. For example, the other audio signal may not be configured to provide user feedback. More specifically, the other audio signal may be, for example, media audio (e.g., music, radio, or movie audio) or conversational audio (e.g., a telephone call) unconnected with the feedback audio. The other audio signal may be sent concurrently with the feedback signal. In other words, the headphone device may be actively emitting audible sound, such as during conventional use of a headphone for purposes of listening to music, voice, or other audible sounds, and, at the same time, the headphone may be used to provide haptic feedback to the user by actuating one or more one or more tactile bass vibrators of the headphone responsive to receipt of the feedback signal by the one or more tactile base vibrators from the computing device.

The method 100 may further involve generating a tactile vibration utilizing the tactile bass vibrator of the headphone device in response to the feedback signal, as indicated at action 104. The tactile vibration may be of an amplitude such that vibrations generated by the tactile bass vibrator are felt by a user wearing the headphone device, giving the user feedback associated with the tactile vibration. In addition, the tactile bass vibrator may produce some audible sound in addition to the tactile vibration. For example, the tactile bass vibrator may produce audible sound at bass frequencies. More specifically, the tactile bass vibrator may produce audible sound at low bass frequencies. The primary mechanism for giving the user feedback may be tactile. The audible sound generated in connection with the tactile vibration may be incidental to the vibratory sensation that is the primary means of sending feedback to the user.

The tactile vibration may be generated by the tactile bass vibrator of the headphone device in, for example, a predetermined vibration pattern. More specifically, the tactile vibration generated by the tactile bass vibrator of the headphone device may be, for example, a burst of vibratory tactile feedback at a predetermined frequency (e.g., a bass frequency or a low bass frequency) or a series of bursts of vibratory tactile feedback. As a specific, nonlimiting example, the tactile vibration generated by the tactile bass vibrator of the headphone device may be a predetermined series of bursts of vibratory tactile feedback separated by a predetermined series of rests between bursts, during which no vibratory tactile feedback associated with the feedback signal is generated.

In some embodiments, the predetermined vibration pattern of the tactile vibration generated by the tactile bass vibrator of the headphone device may be customizable by the user. For example, the predetermined vibration pattern for a particular notification to be sent to the user may be selected from a set of predetermined vibration patterns (and associated feedback signals) stored in memory of the computing device. More specifically, the predetermined vibration pattern for a particular notification to be sent to the user may be selected from a set of audio files composed of bass frequency waves stored in memory of the computing device. As a specific, nonlimiting example, the predetermined vibration pattern for a particular notification to be sent to the user may be selected from a set of audio files composed of low bass frequency waves stored in memory of the computing device. As another example of customizable vibration patterns, the predetermined vibration pattern may be defined by a user in response to user input at the computing device. More specifically, user interaction with a user input device (e.g., a button, switch, touchscreen, etc.) of the computing device may define the amplitude, frequency, duration, or any combination of amplitude, frequency, and duration of bursts of vibratory tactile feedback as well as the duration of rests between bursts, during which no vibratory tactile feedback associated with the feedback signal is generated.

As previously mentioned, audible sound may be generated by speakers (e.g., audio drivers) of the headphone device concurrently as tactile vibration is generated by the tactile bass vibrators. For example, audible sound corresponding to an audio signal may be generated by the speakers, and optionally by the tactile bass vibrators, while tactile vibrations corresponding to a feedback signal may be generated by the tactile bass vibrators alone. More specifically, the speakers, and optionally the tactile bass vibrators, may play, for example, media audio or telephone call audio at the same time as the tactile bass vibrators generate tactile vibrations.

Because the feedback given to the user by the tactile bass vibrators is felt, and optionally heard, as opposed to solely being heard, solely being seen, or being heard and seen, the feedback may be less intrusive than conventional feedback from computing devices. Moreover, the tactile feedback given to the user may not interrupt the experience of the user using the computing device (e.g., may not interrupt the audio played by the speakers, and optionally by the tactile bass vibrators) because its primary communication mechanism may be tactile, rather than aural or visual.

As one example of generating tactile feedback for a user while using the headphone device and computing device, a user may wear the headphone device connected to a computing device (e.g., a smartphone or fitness band wirelessly connected to a smartphone) while engaging in physical exercise (e.g., running, cycling, hiking, etc.). The fitness band may include a heart rate monitor, and information from the heart rate monitor may be sent from the fitness band to the smartphone for storage and processing. The smartphone may include a GPS unit and other wireless signal transceivers for generation and processing of location data.

The user may listen to one or more audio files (e.g., music, audiobooks, or radio programming, such as podcasts) while engaging in the physical exercise. The headphone device may produce audible sound and tactile vibrations in response to receiving the audio signals associated with the audio files.

When an event relating to the physical exercise has occurred, such as, for example, a user's heart rate entering a desired range or the user traveling a predetermined distance, a feedback signal may be sent from the computing device to the headphone device. The feedback signal may cause the headphone device to generate tactile vibrations distinct from the tactile vibrations generated in response to the audio signal, such as, for example, a series of short bursts of vibration. Depending on the specific pattern of the tactile vibrations and the predetermined semantic meaning assigned to the specific pattern of the tactile vibrations, the user may understand that his or her heart rate has entered a desired range, he or she has traveled a predetermined distance (e.g., a notification for each mile traveled), or that he or she has maintained a predetermined pas over the predetermined distance. As specific, nonlimiting examples, the headphone device may produce two short bursts of vibration, followed by a brief pause, followed by two additional short bursts of vibration (e.g., mimicking a heartbeat) to indicate that the user's heart rate has entered a desired range; may produce a single, sustained burst of vibration followed by a pause for each mile traveled since the physical exercise began; and may produce a single, sustained burst of vibration followed by a pause for each mile traveled since the physical exercise began followed by a short burst of vibration for each minute passed during the most recent mile, each of which may occur while the headphone device simultaneously generates the audible sound and tactile vibrations in response to the audio signal.

As another example of generating tactile feedback for a user while using the headphone device and computing device, a user may wear the headphone device connected to a computing device (e.g., a smartphone or in-car infotainment system) while navigating (e.g., while walking, cycling, or driving) to a desired destination. The smartphone or in-car infotainment system may include a GPS unit and other wireless signal transceivers for generation and processing of location data.

The user may listen to one or more audio files (e.g., music, audiobooks, or radio programming, such as podcasts) while navigating. The headphone device may produce audible sound and tactile vibrations in response to receiving the audio signals associated with the audio files.

When an event relating to the navigation has occurred, such as, for example, a user approaching a required deviation from the path (e.g., a turn or lane change) to continue toward the destination or a user reaching the destination, a feedback signal may be sent from the computing device to the headphone device. The feedback signal may cause the headphone device to generate tactile vibrations distinct from the tactile vibrations generated in response to the audio signal, such as, for example, a series of short bursts of vibration. Depending on the specific pattern of the tactile vibrations and the predetermined semantic meaning assigned to the specific pattern of the tactile vibrations, the user may understand that he or she should turn right or left at the next intersection, he or she should merge right or left before the next highway lane event (e.g., interchange, exit, entrance, etc.), or he or she should stop at the destination. As specific, nonlimiting examples, the headphone device may produce two short bursts of vibration in a left-side or right-side ear cup to indicate that the user should turn left or right at the next intersection; may produce one sustained burst of vibration in a left-side or right-side ear cup to indicate that the user should merge left or right before the next highway lane event; and may produce three, sustained bursts of vibration to indicate that the user is approaching or has reached the destination, each of which may occur while the headphone device simultaneously generates the audible sound and tactile vibrations in response to the audio signal.

As yet another example of generating tactile feedback for a user while using the headphone device and computing device, a user may wear the headphone device connected to a computing device (e.g., a smartphone, portable video game console, or fitness tracker connected to a smartphone) while participating in adventure sports (e.g., snowboarding, skiing, skydiving, etc.). The computing device may include a GPS unit and other wireless signal transceivers for generation and processing of location data and the computing device or a peripheral device connected to the computing device may include an altimeter for generation and processing of altitude data.

The user may listen to one or more audio files (e.g., music, audiobooks, or radio programming, such as podcasts) while participating in the adventure sport. The headphone device may produce audible sound and tactile vibrations in response to receiving the audio signals associated with the audio files.

When an event relating to the adventure sport has occurred, such as, for example, a user crossing an altitude threshold (e.g., after which it is advisable to deploy a parachute), a feedback signal may be sent from the computing device to the headphone device. The feedback signal may cause the headphone device to generate tactile vibrations distinct from the tactile vibrations generated in response to the audio signal, such as, for example, a series of short bursts of vibration. Depending on the specific pattern of the tactile vibrations and the predetermined semantic meaning assigned to the specific pattern of the tactile vibrations, the user may understand that he or she should deploy a parachute. As specific, nonlimiting examples, the headphone device may produce five short bursts of vibration interspersed by long pauses to indicate that the user has crossed an upper threshold for deploying a parachute; may produce five short bursts of vibration interspersed by medium-length pauses to indicate that the user has crossed an middle threshold for deploying a parachute; and may produce five short bursts of vibration interspersed by short pauses to indicate that the user has crossed a lowest threshold for deploying a parachute, each of which may occur while the headphone device simultaneously generates the audible sound and tactile vibrations in response to the audio signal.

Figure 2:
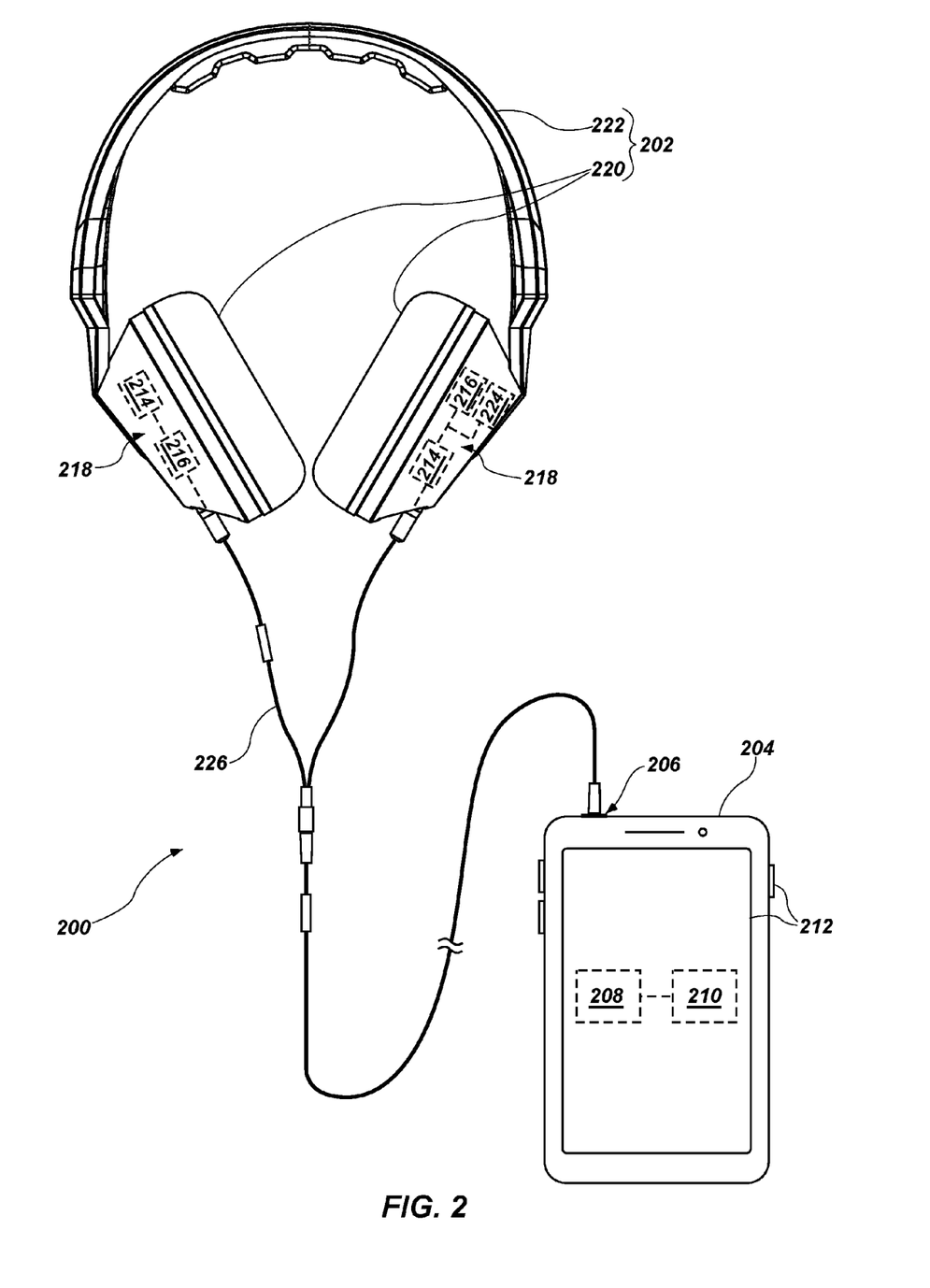
FIG. 2 is a simplified view of a system for generating tactile user feedback utilizing a headphone device according to the present disclosure.

FIG. 2 is a simplified view of a system 200 for generating tactile user feedback utilizing a headphone device 202. The system 200 may include a computing device 204 connected to the headphone device 202. The computing device 204 may be any device configured for connecting to the headphone device 202, determining when to send a feedback signal, and sending the feedback signal or signals. For example, the computing device 204 may include an audio connector 206 (e.g., a female audio jack, a wireless connector, such as, for example, BLUETOOTH®, etc.), a control circuit 208 (e.g., a processor), a memory device 210 (e.g., flash memory), and user input devices 212 (e.g., a touchscreen, buttons, switches, etc.). As specific, nonlimiting examples, the computing device 204 may be a tablet device, a smartphone, a video game console (e.g., a portable video game console), or an in-car infotainment system.

The headphone device 202 may include one or more speakers 214 and one or more tactile bass vibrators 216. For example, the headphone device 202 may include left-side and right-side speakers 214 and left-side and right-side tactile bass vibrators 216. The speakers 214 may be distinct from the tactile bass vibrators 216.

The left-side and right-side speakers 214 and left-side and right-side tactile bass vibrators 216 may be configured as, for example, over-the-ear, on-ear, in-concha, or in-ear earphones. The left-side and right-side speakers 214 and left-side and right-side tactile bass vibrators 216 may be located within housings 218 of the headphone device 202. The left-side and right-side speakers 214 may be configured to generate audible sound in response to audio signals sent from the computing device 204 to the headphone device 202. The left-side and right-side speakers 214 may not generate any audible sound or any tactile vibration in response to feedback signals sent from the computing device 204 to the headphone device. The left-side, right-side, or left-side and right-side tactile bass vibrators 216 may be configured to generate audible sound and tactile vibrations in response to audio signals and feedback signals sent from the computing device 204 to the headphone device 202.

In embodiments where the headphone device 202 exhibits an over-the-ear or an on-ear configuration, the housings 218 may define left-side and right-side ear cups 220 of the headphone device 202. In such embodiments, the headphone device 202 may include a headband 222 supporting the ear cups 220 and size and shaped to rest on a user's head, and position the ear cups 220 proximate (e.g., over or on) the user's ears, when using the headphone device 202.

In some embodiments, the headphone device 202 may include an amplifier 224 operatively connected to the tactile bass vibrators 216. The amplifier 224 may be powered separately from the computing device 204. The amplifier 224 may be located, for example, within the one of the housings 218 of the headphone device 202, or an amplifier may be located in each housing 218 of the headphone device 202. As another example, the amplifier 224 may be located in-line with an audio cable 226 connecting the headphone device 202 to the computing device 204.

Suitable headphone devices incorporating tactile bass vibrators 216 are disclosed in U.S. Patent App. Pub. No. 2014/0056459, published Feb. 27, 2014, and titled "SPEAKERS, HEADPHONES, AND KITS RELATED TO VIBRATIONS IN AN AUDIO SYSTEM, AND METHODS FOR FORMING SAME," the disclosure of which was previously incorporated into this application in its entirety by reference. In addition, suitable headphone devices are commercially available from Skullcandy, Inc., of Park City, Utah, under the trademark SKULLCRUSHERS®.

Figure 3:
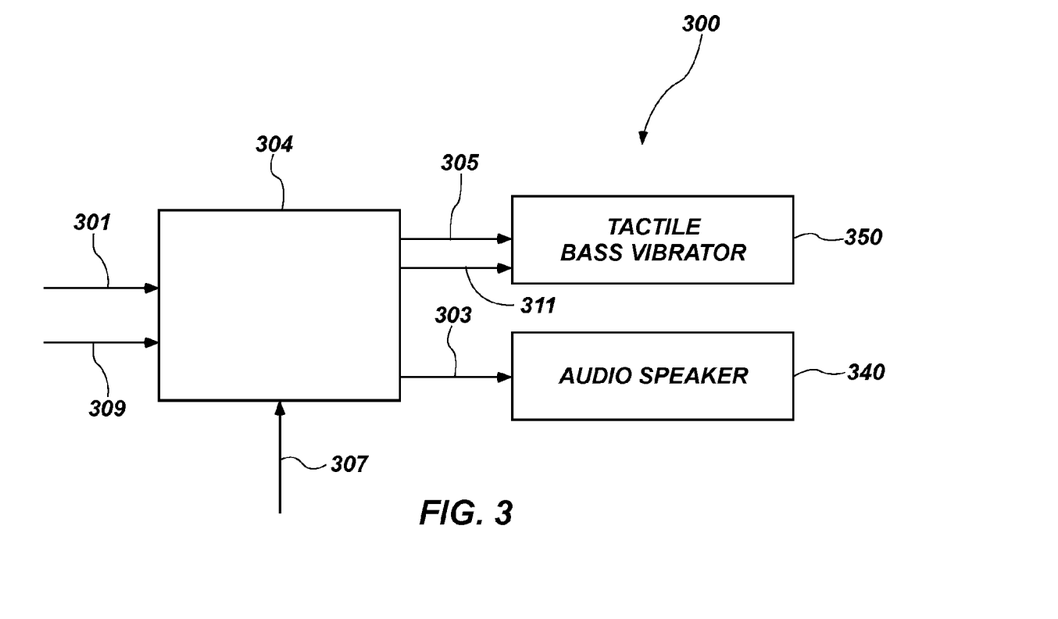
FIG. 3 is a simplified block diagram of a driver system of the headphone device of FIG. 2.

FIG. 3 is a simplified block diagram of a driver system 300 of the headphone device 202 of FIG. 2. The driver system 300 may be located within housings 218 of the ear cups 220 of the headphone device 202 of FIG. 2 to convert audio signals 301 to audible sound and a tactile response and feedback signals 309 to a tactile response and optionally audible sound. The driver system 300 may include a speaker 340 (e.g., an audio driver) configured to emit sound at audible frequencies, and an additional, distinct tactile bass vibrator 350 configured to emit audible sound at bass frequencies (e.g., low bass frequencies) and to generate tactile vibrations within the speaker assemblies ear cups 220 that may be felt by the user. The driver system 300 may include a signal splitter/controller 304 configured to receive audio signals 301 and feedback signals 309 (e.g., from the computing device (FIG. 3)), and transmit a first split audio signal 303 to the audio driver 340 and a second split audio signal 305 and a feedback signal 311 to the tactile bass vibrator 350. The signal splitter 304 may include filters (e.g., low-pass, high-pass, etc.) such that the first split audio signal 303 includes medium to high frequencies (i.e., non-bass frequencies), while the second split audio signal 405 and the feedback signal 311 include the bass frequencies (including low bass frequencies). In some embodiments, at least some of the frequencies of the first split audio signal 303 and the second split audio signal 305 may at least partially overlap. For example, the audio driver 340 may be configured to emit some bass frequencies that are further enhanced by the tactile bass vibrator 350. In some embodiments, none of the frequencies of the first split audio signal 303 and the feedback signal 311 may overlap. For example, the audio driver 340 may be configured not to emit any low bass frequencies that are emitted by the tactile bass vibrator 350 as tactile vibrations.

The signal splitter/controller 304 may further include control logic configured to modify the split audio signals 303 and 305, and optionally the feedback signal 311, responsive to a control signal 307. For example, the control signal 307 may control characteristics, such as volume. The signal splitter/controller 304 may be configured to control the first split audio signal 303, the second split audio signal 405, and optionally the feedback signal 311 independently. For example, a user may desire louder bass frequencies and a stronger tactile response at the bass frequencies, or a user may desire more intense, detectable haptic feedback relative to the volume of audio. As a result, more power may be supplied to the tactile bass vibrator 450 relative to the power supplied to the audio driver 440.

The various illustrative logical blocks, modules, circuits, and algorithm acts described in connection with embodiments disclosed herein may be implemented or performed with one or more control circuits such as a general-purpose processor, a special-purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein.

A general-purpose processor may be a microprocessor, but in the alternative, the general-purpose processor may be any processor, controller, microcontroller, or state machine suitable for carrying out processes of the present disclosure. A processor may also be implemented as a combination of computing devices, such as a combination of a DSP and a microprocessor, a plurality of microprocessors, one or more microprocessors in conjunction with a DSP core, or any other such configuration.

A general-purpose processor may be part of a general-purpose computer, which should be considered a special-purpose computer when configured to execute computing instructions (e.g., software code) for carrying out embodiments of the present disclosure. Moreover, when configured according to embodiments of the present disclosure, such a special-purpose computer improves the function of a general-purpose computer because, absent the present disclosure, the general-purpose computer would not be able to carry out the processes of the present disclosure. The present disclosure also provides meaningful limitations in one or more particular technical environments that go beyond an abstract idea. For example, embodiments of the present disclosure provide improvements in the technical field of haptic feedback generation and provision.

Additional, illustrative embodiments within the scope of this disclosure include the following:

Embodiment 1

A method of generating tactile user feedback utilizing a headphone device, comprising: sending a feedback signal from a computing device to a headphone device operatively connected to the computing device; and generating a tactile vibration utilizing a tactile bass vibrator of the headphone device in response to the feedback signal.

Embodiment 2

The method of claim 1, further comprising: sending an audio signal from the computing device to the headphone device; and generating audible sound utilizing a speaker of the headphone in response to the audio signal, the speaker being distinct from the tactile bass vibrator.

Embodiment 3

The method of claim 2, wherein the feedback signal is sent concurrently with the audio signal and the tactile vibration is generated concurrently with the audible sound.

Embodiment 4

The method of any one of Embodiments 1 through 3, wherein sending the feedback signal from the computing device to the headphone device comprises sending a feedback signal composed of bass frequency waves from the computing device to the headphone device.

Embodiment 5

The method of any one of Embodiments 1 through 4, wherein sending the feedback signal from the computing device to the headphone device comprises sending the feedback signal from the computing device to the headphone device in response to a user input received at the computing device.

Embodiment 6

The method of any one of Embodiments 1 through 5, wherein generating the tactile vibration utilizing the tactile bass vibrator of the headphone device in response to the feedback signal comprises generating a tactile vibration in a predetermined vibration pattern utilizing the tactile bass vibrator.

Embodiment 7

The method of Embodiment 6, further comprising selecting the predetermined vibration pattern from a set of predetermined vibration patterns stored in memory of the computing device.

Embodiment 8

The method of Embodiment 6, further comprising defining the predetermined vibration pattern in response to user input at the computing device.

Embodiment 9

The method of any one of Embodiments 1 through 4 and 6 through 8, wherein sending the feedback signal from the computing device to the headphone device comprises sending the feedback signal in response to at least one of: a signal relating to physical activity of the user; a signal relating to navigation for the user; and a signal relating to an adventure sport engaged in by the user.

Embodiment 10

The method of Embodiment 9, wherein: sending the feedback signal from the computing device to the headphone device comprises sending the feedback signal in response to a signal that the user is to turn in the predetermined direction generated by the computing device; and generating the tactile vibration utilizing the tactile bass vibrator of the headphone device in response to the feedback signal comprises generating the tactile vibration in a left-side tactile bass vibrator or a right-side tactile bass vibrator of the headphone device corresponding to the predetermined direction in which the user is to turn.

Embodiment 11

A system for generating tactile user feedback utilizing a headphone device, comprising: a headphone device operatively connected to a computing device, the headphone device comprising a tactile bass vibrator configured to generate a tactile vibration in response to a feedback signal received from the computing device; wherein the computing device is programmed to send a feedback signal to the headphone device in response to a predetermined event.

Embodiment 12

The system of Embodiment 11, wherein the headphone device comprises a speaker distinct from the tactile bass vibrator and the computing device is programmed to send an audio signal from the computing device to the headphone device, causing the speaker of the headphone to generate audible sound in response to the audio signal.

Embodiment 13

The system of Embodiment 12, wherein the computing device is programmed to send the feedback signal concurrently with the audio signal, causing the tactile vibration to be generated concurrently with the audible sound.

Embodiment 14

The system of any one of Embodiments 11 through 13, wherein the computing device is programmed to send a feedback signal composed of bass frequency waves from the computing device to the headphone device.

Embodiment 15

The system of any one of Embodiments 11 through 14, wherein the computing device is programmed to send the feedback signal to cause the tactile bass vibrator of the headphone device to generate the tactile vibration in a predetermined vibration pattern.

Embodiment 16

The system of any one of Embodiments 11 through 15, wherein the computing device is programmed to send the feedback signal from the computing device to the headphone device comprises sending the feedback signal in response to at least one of: a signal relating to physical activity of the user; a signal relating to navigation for the user; and a signal relating to an adventure sport engaged in by the user.

Embodiment 17

The system of any one of Embodiments 11 through 16, wherein the headphone device comprises a left-side tactile bass vibrator and a right-side tactile bass vibrator located within housings corresponding to a left-side ear cup and a right-side ear cup of the headphone device.

Embodiment 18

The system of Embodiment 17, wherein the computing device is programmed to send the feedback signal from the computing device to the headphone device in response to a signal that the user is to turn in the predetermined direction generated by the computing device, causing the tactile bass vibrator of the headphone device to generate the tactile vibration in the left-side tactile bass vibrator or the right-side tactile bass vibrator of the headphone device corresponding to the predetermined direction in which the user is to turn.

Embodiment 19

The system of any one of Embodiments 11 through 18, wherein the computing device is at least one of a tablet device, a smartphone, a video game console, and an in-car infotainment system.

Embodiment 20

The system of any one of Embodiments 11 through 19, wherein the headphone device comprises an amplifier located within a housing of the headphone device, the amplifier being operatively connected to the tactile bass vibrator of the headphone device.

While certain illustrative embodiments have been described in connection with the figures, those of ordinary skill in the art will recognize and appreciate that the scope of this disclosure is not limited to those embodiments explicitly shown and described in this disclosure. Rather, many additions, deletions, and modifications to the embodiments described in this disclosure may result in embodiments within the scope of this disclosure, such as those specifically claimed, including legal equivalents. In addition, features from one disclosed embodiment may be combined with features of another disclosed embodiment while still being within the scope of this disclosure, as contemplated by the inventors.

What is claimed is:

1. A method of generating tactile user feedback utilizing a headphone device, comprising:
sending a feedback signal from a computing device to a headphone device operatively connected to the computing device in response to an input generated by the computing device or by another device operatively connected to the computing device, the feedback signal being distinct from any audio signal associated with media playback and conversational audio sent from the computing device to the headphone device; and
generating a tactile vibration utilizing a tactile bass vibrator of the headphone device in response to the feedback signal.

2. The method of claim 1, further comprising:
sending an audio signal associated with media playback or conversational audio from the computing device to the headphone device; and
generating audible sound utilizing a speaker of the headphone in response to the audio signal, the speaker being distinct from the tactile bass vibrator.

3. The method of claim 2, wherein the feedback signal is sent concurrently with the audio signal and the tactile vibration is generated concurrently with the audible sound.

4. The method of claim 1, wherein sending the feedback signal from the computing device to the headphone device comprises sending a feedback signal composed of bass frequency waves from the computing device to the headphone device.

5. The method of claim 1, further comprising sending another feedback signal from the computing device to the headphone device in response to a user input received at the computing device.

6. The method of claim 1, wherein generating the tactile vibration utilizing the tactile bass vibrator of the headphone device in response to the feedback signal comprises generating a tactile vibration in a predetermined vibration pattern utilizing the tactile bass vibrator.

7. The method of claim 6, further comprising selecting the predetermined vibration pattern from a set of predetermined vibration patterns stored in memory of the computing device.

8. The method of claim 6, further comprising defining the predetermined vibration pattern in response to user input at the computing device.

9. The method of claim 1, wherein sending the feedback signal from the computing device to the headphone device in response to the input generated by the computing device or by another device operatively connected to the computing device comprises sending the feedback signal in response to at least one of:

a signal relating to physical activity of the user generated by the computing device or by another device operatively connected to the computing device;

a signal relating to navigation for the user generated by the computing device or by another device operatively connected to the computing device; and a signal relating to an adventure sport engaged in by the user generated by the computing device or by another device operatively connected to the computing device.

10. The method of claim 9, wherein:

sending the feedback signal from the computing device to the headphone device comprises sending the feedback signal in response to a signal that the user is to turn in the predetermined direction generated by the computing device; and generating the tactile vibration utilizing the tactile bass vibrator of the headphone device in response to the feedback signal comprises generating the tactile vibration in a left-side tactile bass vibrator or a right-side tactile bass vibrator of the headphone device corresponding to the predetermined direction in which the user is to turn.

11. A system for generating tactile user feedback utilizing a headphone device, comprising:

a headphone device operatively connected to a computing device, the headphone device comprising a tactile bass vibrator configured to generate a tactile vibration in response to a feedback signal received from the computing device;

wherein the computing device is programmed to automatically generate and send a feedback signal to the headphone device in response to the occurrence of a predetermined event the feedback signal being distinct from any audio signal associated with media playback and conversational audio sent from the computing device to the headphone device.

12. The system of claim 11, wherein the headphone device comprises a speaker distinct from the tactile bass vibrator and the computing device is programmed to send an audio signal associated with media playback or conversational audio from the computing device to the headphone device, causing the speaker of the headphone to generate audible sound in response to the audio signal.

13. The system of claim 12, wherein the computing device is programmed to send the feedback signal concurrently with the audio signal, causing the tactile vibration to be generated concurrently with the audible sound.

14. The system of claim 11, wherein the computing device is programmed to send a feedback signal composed of bass frequency waves from the computing device to the headphone device.

15. The system of claim 11, wherein the computing device is programmed to send the feedback signal to cause the tactile bass vibrator of the headphone device to generate the tactile vibration in a predetermined vibration pattern.

16. The system of claim 11, wherein the computing device is programmed to automatically generate and send the feedback signal from the computing device to the headphone device in response to the occurrence of at least one of:

a signal relating to physical activity of the user generated by the computing device;

a signal relating to navigation for the user generated by the computing device; and a signal relating to an adventure sport engaged in by the user generated by the computing device.

17. The system of claim 16, wherein the headphone device comprises a left-side tactile bass vibrator and a right-side tactile bass vibrator located within housings corresponding to a left-side ear cup and a right-side ear cup of the headphone device.

18. The system of claim 17, wherein the computing device is programmed to send the feedback signal from the computing device to the headphone device in response to a signal that the user is to turn in the predetermined direction generated by the computing device, causing the tactile bass vibrator of the headphone device to generate the tactile vibration in the left-side tactile bass vibrator or the right-side tactile bass vibrator of the headphone device corresponding to the predetermined direction in which the user is to turn.

19. The system of claim 11, wherein the computing device is at least one of a tablet device, a smartphone, a video game console, and an in-car infotainment system.

20. The system of claim 11, wherein the headphone device comprises an amplifier located within a housing of the headphone device, the amplifier being operatively connected to the tactile bass vibrator of the headphone device.

* * * * *

UNITED STATES PATENT AND TRADEMARK OFFICE
CERTIFICATE OF CORRECTION

PATENT NO.       : 9,712,907 B2                                      Page 1 of 1
APPLICATION NO.  : 14/982647
DATED            : July 18, 2017
INVENTOR(S)      : Sam Noertker, John Timothy and Matthew Windt It is certified that error appears in the above-identified patent and that said Letters Patent is hereby corrected as shown below:

In the Specification

| | | |
|---|---|---|
| Column 5, | Line 50, | change "predetermined pas over" to --predetermined pace over-- |
| Column 7, | Line 49, | change "headphone device." to --headphone device **202**.-- |
| Column 7, | Line 59, | change "and size and" to --and sized and-- |
| Column 8, | Line 30, | change "computing device" to --computing device **204**-- |
| Column 8, | Line 30, | change "(FIG. 3), and" to --(FIG. 2), and-- |
| Column 8, | Line 36, | change "audio signal **405** and" to --audio signal **305** and-- |
| Column 8, | Line 55, | change "audio signal **405**," to --audio signal **305**,-- |
| Column 8, | Line 61, | change "vibrator **450** relative" to --vibrator **350** relative-- |
| Column 8, | Line 62, | change "audio driver **440**." to --audio driver **340**.-- |

Signed and Sealed this
Twenty-third Day of January, 2018

Joseph Matal
*Performing the Functions and Duties of the
Under Secretary of Commerce for Intellectual Property and
Director of the United States Patent and Trademark Office*